(12) United States Patent
Satou et al.

(10) Patent No.: US 7,781,204 B2
(45) Date of Patent: Aug. 24, 2010

(54) METHOD FOR ANALYZING A BIOCHIP

(75) Inventors: Saya Satou, Musashino (JP); Takeo Tanaami, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 681 days.

(21) Appl. No.: 11/519,809

(22) Filed: Sep. 13, 2006

(65) Prior Publication Data

US 2007/0065855 A1    Mar. 22, 2007

(30) Foreign Application Priority Data

Sep. 21, 2005    (JP) .............................. 2005-273076

(51) Int. Cl.
*C12M 1/34* (2006.01)
*C12M 3/00* (2006.01)

(52) U.S. Cl. ...................... 435/287.2; 435/6; 435/288.7

(58) Field of Classification Search ..................... 435/6, 435/287.2, 288.7
See application file for complete search history.

(56) References Cited

U.S. PATENT DOCUMENTS

| 2003/0170672 | A1  | 9/2003 | Cho et al. |
| 2005/0106613 | A1* | 5/2005 | Ishibashi ........................ 435/6 |
| 2005/0170332 | A1* | 8/2005 | Shimamoto ..................... 435/4 |

FOREIGN PATENT DOCUMENTS

| JP | 2001-78766 A | 3/2001 |
| WO | WO 03/003021 A1 | 1/2003 |
| WO | WO 2004/017374 A2 | 2/2004 |

OTHER PUBLICATIONS

Extended European Search Report dated Feb. 12, 2007, issued in corresponding European Application No. 06017988.4.

* cited by examiner

*Primary Examiner*—Walter D Griffin
*Assistant Examiner*—Shanta G Doe
(74) *Attorney, Agent, or Firm*—Westerman, Hattori, Daniels & Adrian, LLP

(57) ABSTRACT

There is provided a biochip capable of quantitatively grasping hybridization efficiency. In the biochip comprising a plurality of probe sites with target molecules bonded thereto, respectively, the probe sites disposed thereon, the marker sites with a known number of fluorescent molecules bonded thereto, respectively, are disposed. With the biochip, the number of the fluorescent molecules bonded to the respective marker sites is already known, so that respective hybridization efficiencies at the probe sites can be quantitatively grasped by comparing respective intensity of fluorescent light of the probe sites with an intensity of fluorescent light of the marker sites. The fluorescent molecule may be bonded to the respective marker sites when the biochip is formed, or the respective marker sites may be made up such that the fluorescent molecule of a predetermined molecular weight is bonded thereto by a predetermined processing applied to the biochip. The respective marker sites may be formed by use of a biopolymer of the same species as that for the respective probe sites.

2 Claims, 4 Drawing Sheets

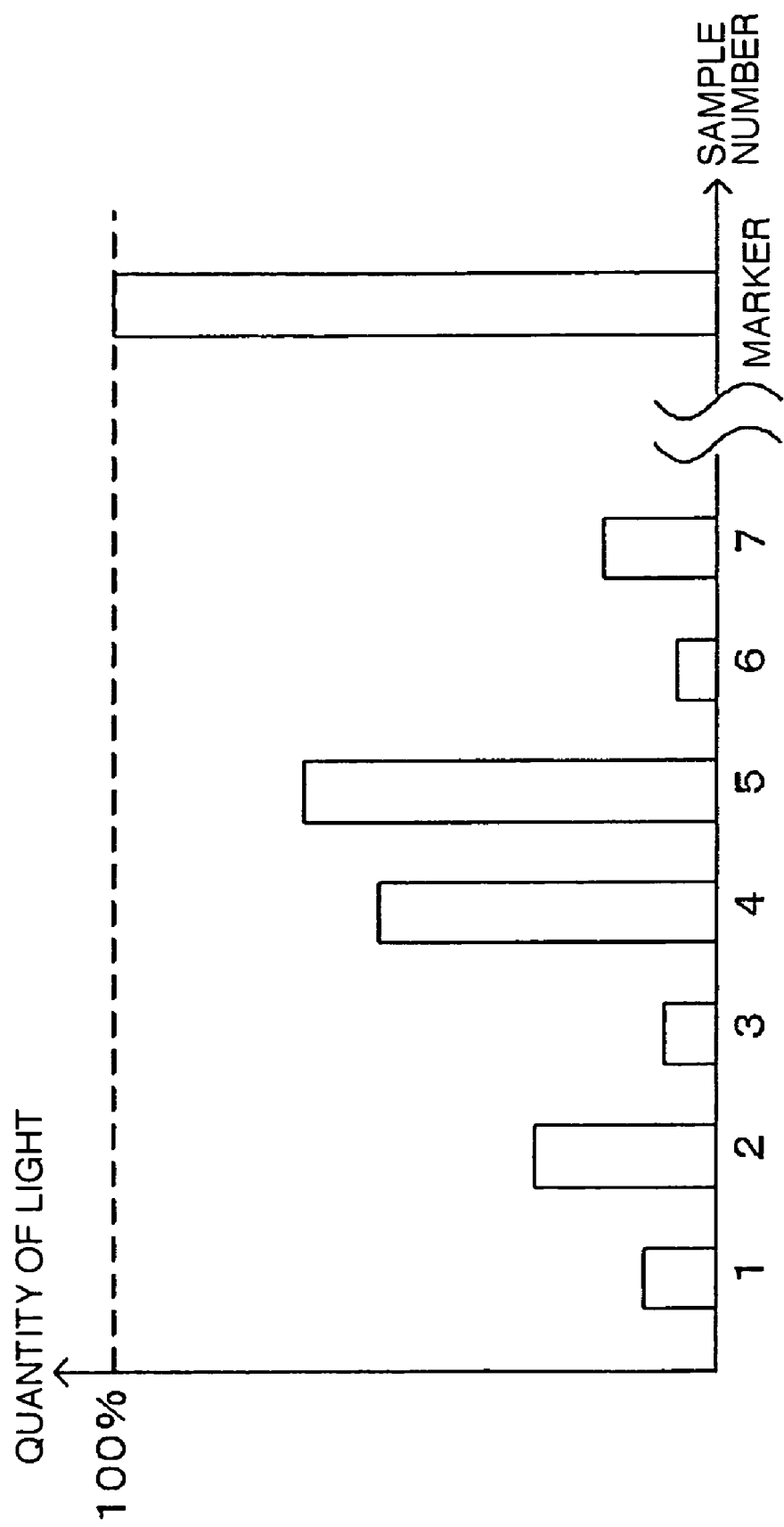

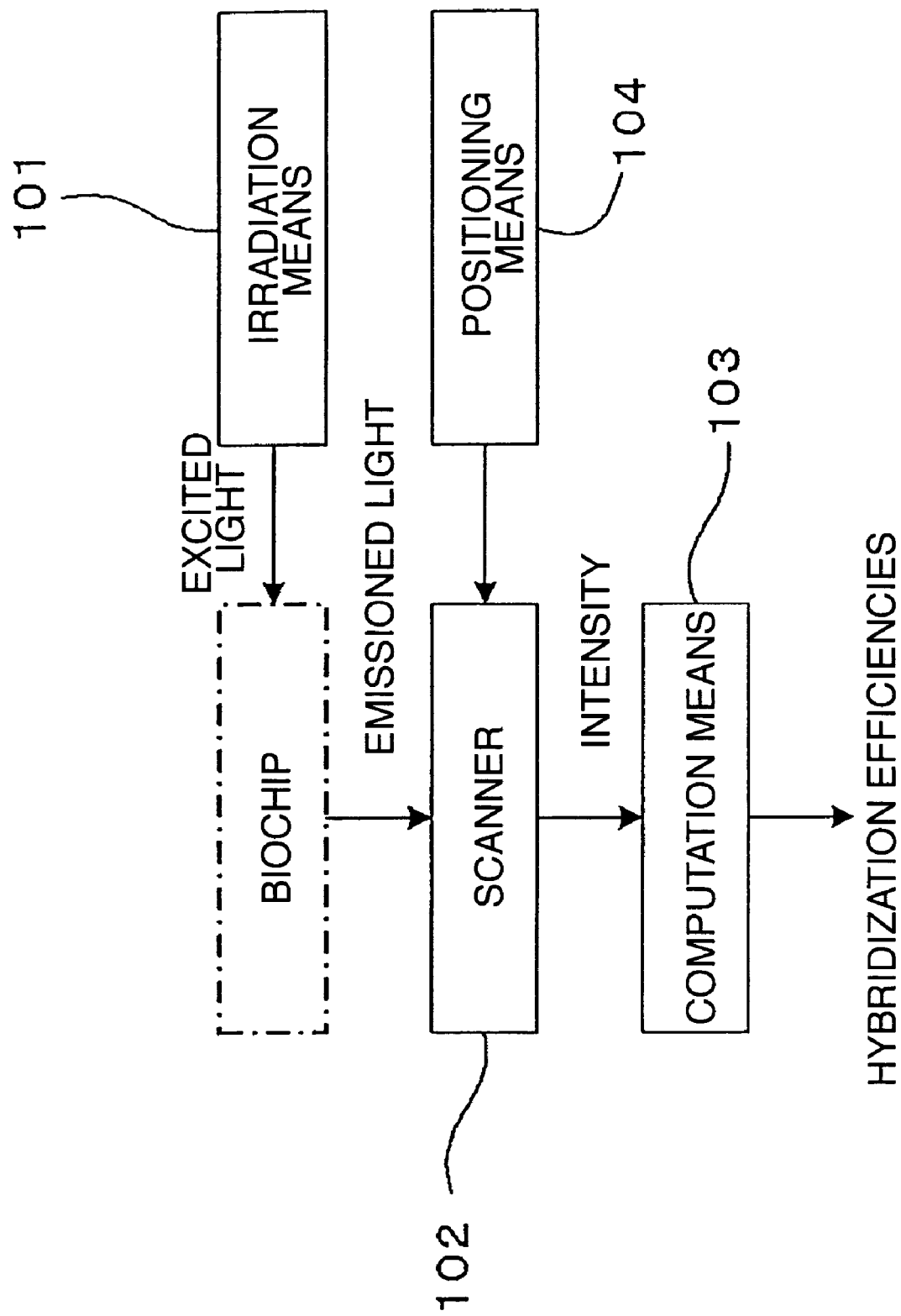

METHOD FOR ANALYZING A BIOCHIP

FIELD OF THE INVENTION

The invention relates to a biochip utilizing the principle of hybridization and an analytical instrument for analyzing the biochip.

BACKGROUND OF THE INVENTION

There has been known a biochip utilizing the principle of hybridization whereby complementary bases are singularly bonded with each other. On the biochip, there are disposed probe sites to which probe DNA respectively coupled with target DNA, and the target DNA is hydrogen-bonded to the probe sites corresponding thereto, respectively, by hybridization. The efficiency of hybridization, that is, a quantity of the target DNA as bonded can be measured by use of a fluorescent marker (refer to, for example, Patent Document 1).

[Patent Document 1] JP 2001-78766

SUMMARY OF THE INVENTION

A quantity of target DNA coupled with probe sites varies according to the number of the probe DNA at the probe sites. With a conventional biochip, however, there is a problem in that it is impossible to quantitatively grasp hybridization efficiency because the number of the probe DNA at the respective probe sites is unknown.

As a method for quantifying the hybridization efficiency, there is a method used in Code Link Expression Bioarray System (trade name). With this method, after probe sites are formed by spotting, spotted quantity at the respective probe sites are grasped by measuring relative fluorescent intensity of intercalater, and at the time of shipment, a measured value of data is attached.

With this method, however, a ratio of the probe DNA washed away during hybridization processing is unknown, so that it is not possible to work out accurate hybridization efficiency.

It is therefore an object of the invention to provide a biochip capable of quantitatively grasping hybridization efficiency, and an analytical instrument adaptable to the biochip In accordance with one aspect of the invention, there is provided a biochip comprising a plurality of probe sites with target molecules bonded thereto, respectively, the probe sites being disposed thereon, wherein marker sites with a known number of fluorophore-modified molecules bonded thereto, respectively, are disposed.

With the biochip, the number of the fluorophore-modified molecules bonded to the respective marker sites is already known, so that respective hybridization efficiencies at the probe sites can be quantitatively grasped by comparing respective intensity of fluorescent light of the probe sites with an intensity of fluorescent light of the marker sites. The fluorophore-modified molecule may be bonded to the respective marker sites when the biochip is formed, or the respective marker sites may be made up such that the fluorophore-modified molecule of a predetermined molecular weight is bonded thereto by a predetermined processing applied to the biochip.

The respective marker sites may be formed by use of a biopolymer of the same species as that for the respective probe sites.

In such a case, since the respective marker sites are formed by use of the biopolymer of the same species as that for the respective probe sites, it is possible to equalize the amount of the biopolymer given to the respective marker sites to the amount of the biopolymer given to the respective probe sites when forming the biochip. Accordingly, a ratio of an intensity of fluorescent light always correctly indicates hybridization efficiency regardless of conditions at the time when the biochip is formed. Further, as a result of processing applied to the biochip, a ratio of the biopolymers washed away is equalized between the respective marker sites and the respective probe sites, so that the ratio of the intensity of the fluorescent light always correctly indicates the hybridization efficiency regardless of a stage of the processing.

The respective marker sites may be formed by use of a biopolymer equivalent in molecular weight to a biopolymer for the respective probe sites.

In such a case, since the respective marker sites are formed by use of the biopolymer equivalent in molecular weight to the biopolymer for the respective probe sites, it is possible to equalize an amount of the biopolymer given to the respective marker sites and that given to the respective probe sites when forming the biochip. Accordingly, the ratio of the intensity of the fluorescent light always correctly indicates the hybridization efficiency regardless of the conditions at the time when the biochip is formed. Further, the respective marker sites and the respective probe sites are equivalent to each other in the ratio of the biopolymers washed away due to the processing applied to the biochip, so that the ratio of the intensity of the fluorescent light always correctly indicates the hybridization efficiency regardless of the stage of the processing.

A plurality of marker sites differing from each other in quantity of bonded molecules modified with fluorophores may be disposed. In this case, it is possible to grasp the hybridization efficiency over a wide range with stability.

The target molecule may be any selected from the group consisting of DNA, RNA, protein, sugar chain, and metaborome.

In accordance with another aspect of the invention, there is provided an analytical instrument for analyzing a biochip on which a plurality of probe sites with target molecules to be coupled therewith, respectively, and marker sites with a known fluorescent intensity depending on the quantity of molecules, respectively, are disposed, said analytical instrument comprising an irradiation means for irradiating the biochip with excited light, a capturing means for capturing respective intensity of fluorescent light emission from the hybridized sites, and respective intensity of fluorescent light emission from the marker sites, at the time of irradiation of the biochip with the excited light, a measuring means for quantitatively measuring respective hybridization efficiencies of the probe sites by comparing the respective intensity of fluorescent light emission of the probe sites, as captured, with the respective intensity of fluorescent light emission of the marker sites, as captured.

With the analytical instrument, since the number of the fluorescent molecules bonded to the marker sites is already known, the respective hybridization efficiency at the probe sites can be quantitatively grasped by comparing the respective intensity of the fluorescent emission light of the probe sites with the intensity of the fluorescent emission light of the marker sites.

The analytical instrument may further comprise a positioning means for positioning capturing regions of the capturing means on the basis of the fluorescent light from the respective marker sites 3.

With the biochip according to the invention, because the number of the molecules modified with fluorophores bonded to the respective marker sites is already known, the respective hybridization efficiencies at the probe sites can be quantitatively grasped by comparing the respective intensity of the fluorescent light of the probe sites with the intensity of fluorescent light of the marker sites.

Further, with the analytical instrument according to the invention, because the number of the fluorescent molecules bonded to the respective marker sites is already known, the respective hybridization efficiency at the probe sites can be quantitatively grasped by comparing the respective intensity of the fluorescent light of the probe sites with the intensity of the fluorescent light of the marker sites.

BRIEF DESCRIPTION OF THE DRAWINGS

FIG. 3 is a graph showing intensity s of the light of the marker sites 3, and respective intensity of the light of the probe sites 2; and FIG. 4 is a block diagram showing a configuration of one embodiment of an analytical instrument for analyzing the biochip after the hybridization, according to the invention.

PREFERRED EMBODIMENT OF THE INVENTION

Figure 1:
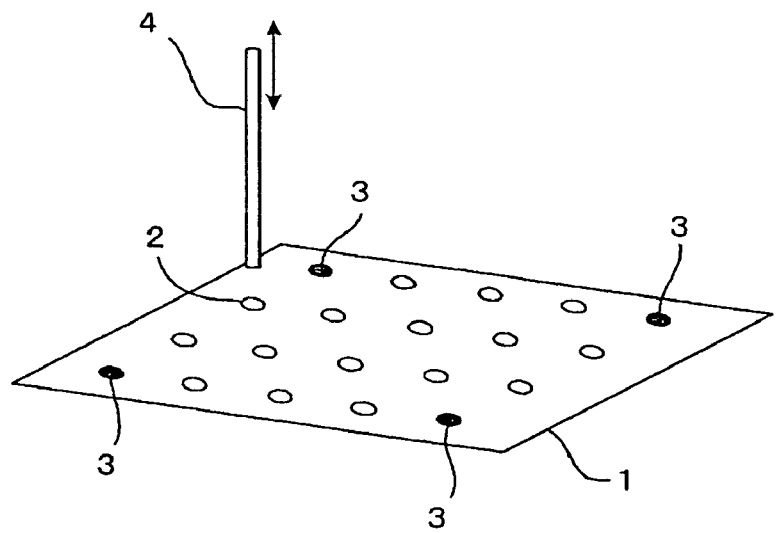
FIG. 1 is a view showing a configuration of a biochip according to one embodiment of the invention, in which FIG. 1 (A) is a perspective view showing the configuration of the biochip according to the embodiment of the invention, FIG. 1 (B) is a schematic illustration showing DNA fixedly attached to a probe site, and fluorophore-modified DNA fixedly attached to a marker site, and FIG. 1 (C) is a view showing the marker sites as recognized.
Figure 1:
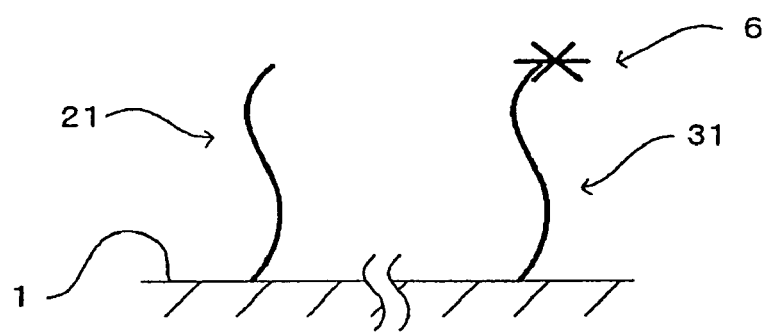
Figure 1:
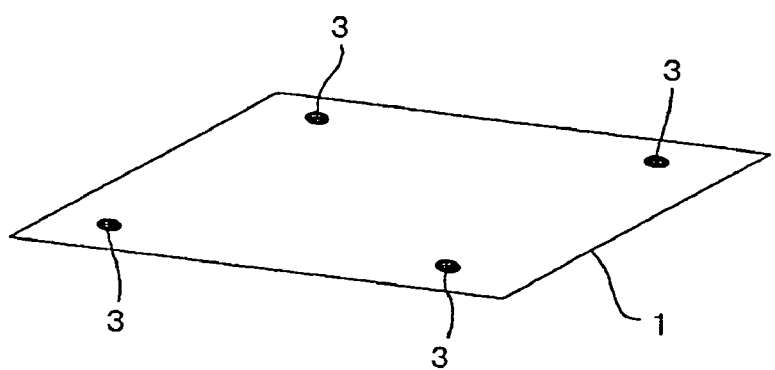

Referring to FIGS. 1 to 3, one embodiment of a biochip according to the invention is described hereinafter.

FIG. 1A is a perspective view showing a configuration of the biochip according to the present embodiment.

As shown in FIG. 1A, the biochip according to the present embodiment comprises a group of probe sites 2 disposed on a substrate 1, for detecting target DNA, and marker sites 3 disposed on the substrate 1, with markers fixedly attached thereto. In FIG. 1A, the marker sites 3 are provided at four corners of the substrate 1, respectively, and the probe site 2 is provided in a matrix fashion at other positions, respectively.

FIG. 1B is a schematic illustration showing DNA fixedly attached to the probe site 2, and the marker site 3, respectively.

As shown in FIG. 1B, a probe DNA 21 for detecting a specific target DNA 6 is fixedly attached to the individual probe sites 2.

Further, a DNA 31 modified with one fluorohore 6 is fixedly attached to the marker site 3.

As shown in FIG. 1A, with the biochip according to the present embodiment, a pin 4 with a predetermined DNA solution adhered thereto is sequentially brought into contact with the substrate 1 to be then spotted, thereby forming the probe sites 2 and the marker sites 3. In this case, by continuously forming the probe sites 2 and the marker sites 3 with the substrate 1 kept in a state as-secured to a stage, it is possible to secure accurate positional relationship between the respective probe sites 2 and the respective marker sites 3.

As shown in FIG. 1C, it is normally impossible to visually identify the probe sites 2. However, with the present embodiment, respective positions of the marker sites 3 can be identified by virtue of light emission of the fluorescent molecules 6, so that it is possible to grasp respective locations of the probe sites 2 on the basis of the respective positions of the marker sites 3.

With the present embodiment, both the probe sites 2 and the marker sites 3 are formed by spotting. Further, by equalizing respective molecularities of DNA to be formed with each other, the DNA solutions spotted at the probe sites 2, and the marker sites 3, respectively, are rendered equivalent to each other in flow characteristics and viscosity. Accordingly, it is possible to render respective quantity of the DNA solution spotted at the probe sites 2, and the DNA solution spotted at the marker sites 3, equivalent to each other. When forming the biochip, a quantity of the DNA solution supplied to the pin 4 generally undergoes variation according to environmental conditions such as temperature, humidity, and so forth. With the present embodiment, however, such variation occurs continuously to the probe sites 2, and the marker sites 3, so that quantity of the respective DNA spotted at the probe sites 2 can be rendered always in agreement with those at the marker sites 3.

With the biochip according to the present embodiment, since the quantity of the respective DNA spotted at the probe sites 2 is in agreement with that at the marker sites 3, it is possible to grasp quantity of DNA spotted at the probe sites 2 by measuring quantity of DNA spotted at the marker sites 3 after the formation of the biochip. The quantity of the DNA spotted at the marker sites 3 can be accurately measured on the basis of a intensity of light emission of the marker sites 3 at the time of irradiation with excited light at a wavelength corresponding to the fluorescent molecule 6.

Further, the DNA of equivalent molecular weight are spotted in equivalent conditions at the probe sites 2, and the marker sites 3, respectively, so that ratios of the DNA washed away from the probe sites 2, and the marker sites 3, respectively, due to processing the biochip, will become equivalent to each other. For this reason, quantity of the probe DNA 21 at the respective probe sites 2, after immobilization processing, washing, or pre-hybridization processing of the target DNA, can be found on the basis of the quantity of the DNA spotted at the marker sites 3, as measured at that point in time.

Figure 2A:
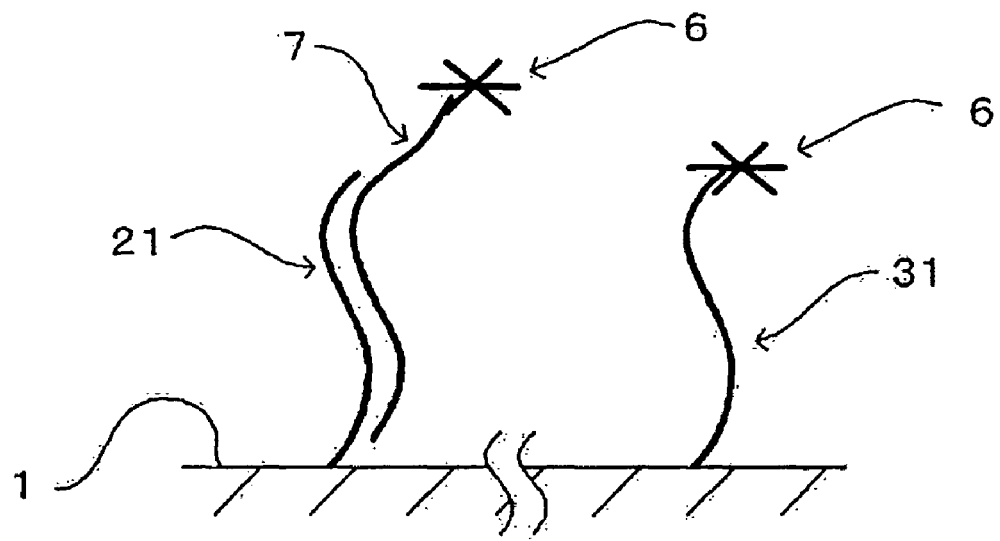
FIG. 2 is a view broadly showing a state of the biochip after hybridization, in which FIG. 2 (A) is a schematic illustration showing the state of the hybridized biochip, and FIG. 2 (B) is a scanned picture showing a state of light emission at the respective sites at the time of irradiation with excited light.
Figure 2B:
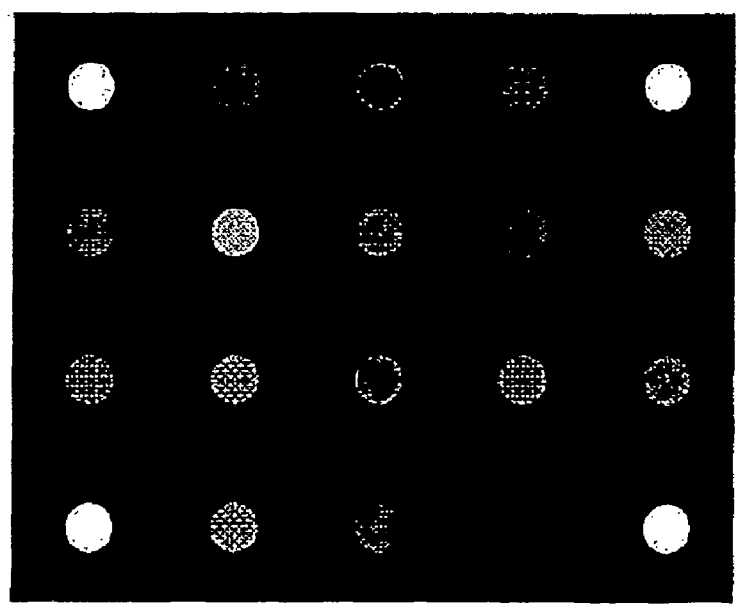

FIG. 2 is a view broadly showing a state of the biochip after hybridization, in which FIG. 2A is a schematic illustration showing the state of the biochip, and FIG. 2B is a scanned picture showing a state of light emission at the respective sites at the time of irradiation with the excited light.

As shown in FIG. 2A, a target DNA 7 with the fluorophore 6 adhered thereto due to hybridization is coupled with the probe DNA 21. When the biochip is irradiated with the excited light after the hybridization, the fluorophores 6 at the respective sites emit light as shown in FIG. 2B. Since an intensity of the light emission corresponds to the number of the fluorophores 6, it is possible to evaluate the number of the fluorophores 6 at the respective probe sites 2 on the basis of the intensity of the light emission of the marker sites 3.

For example, if the fluorophores 6 are kept coupling with the DNA 31 at all the marker sites 3, respectively, intensity of light of the marker sites 3 will correspond to hybridization efficiency of 100%. Accordingly, on the basis of the intensity of the light of the marker sites 3, hybridization efficiencies at the respective probe sites 2 can be quantitatively evaluated.

FIG. 3 is a graph showing the intensity of the light of the marker sites 3, and respective intensity of light of the probe sites 2. In FIG. 3, the intensity of the light of the marker sites 3 corresponds to the hybridization efficiency of 100%, and the respective intensity of the light of the respective probe sites 2, that is, hybridization efficiencies of the respective probe sites 2 are shown as respective absolute values.

FIG. 4 is a block diagram showing a configuration of one embodiment of an analytical instrument for analyzing the biochip after the hybridization, according to the invention.

As shown in FIG. 4, the instrument comprises an irradiation means 101 for irradiating the biochip with excited light, a scanner (capturing means) 102 for capturing respective intensity of fluorescent light emission from the probe sites 2, and respective intensity of fluorescent light emission from the marker sites 3, at the time of irradiation of the biochip with the excited light, a computation means 103 for quantitatively computing the hybridization efficiencies of the respective probe sites 2 by comparing the respective intensity of the fluorescent light emission of the probe sites 2, captured by the scanner 102, with the respective intensity of the fluorescent light emission of the marker sites 3, captured by the scanner 102, and a positioning means 104 for positioning a scanning area of the scanner 102 on the basis of the fluorescent light of the respective marker sites 3.

The respective intensity of the light of the probe sites 2 are captured by photographing the surface of the substrate 1 with the scanner 102. At this point in time, the marker sites 3 each can be used as a reference for positioning by the positioning means 104 when determining a scanning area. Further, on the basis of the respective intensity of the light of the probe sites 2, the computation means 103 computes absolute values of respective hybridization efficiencies. The respective absolute values are computed on the basis of the intensity of the light of the marker sites 3.

With the present embodiment described as above, respective marker concentrations at the marker sites 3 formed at the four corners of the substrate 1 are rendered identical to each other, however, gradation in marker concentration may be provided among a plurality of the marker sites. In such a case, it is possible to stably compute the respective intensity of the light of the probe sites 2, in a wide range of from a low intensity of light emission to a high intensity of light emission, by comparing the respective intensity of the light of the probe sites 2 with that of light emission of the respective marker sites 3. The marker concentration can be controlled by, for example, altering a ratio of DNA modified with the fluorophore to the DNA solution spotted at the respective marker sites 3.

With the present embodiment described as above, there is shown a case where the fluorescent molecule 6 one each is bonded to the DNA 31 at all the marker sites 3, however, for example, two or more of the fluorescent molecules may be bonded thereto provided that the molecularity of the fluorescent molecule can be controlled.

With the present embodiment described as above, a case of detecting DNA is shown by way of example, however, the invention can be applied for detection of various target molecules such as RNA, protein, sugar chain metaborome, and so forth. Further, the invention is not limited in application to a case where detection is executed on a substrate of a biochip, and can be also applied to a biochip of a mesh structure or a structure of three-dimensional gel, and so forth, to which probes are bonded.

With the present embodiment described as above, the intensity of the light emission of the marker sites 3 is set to correspond to the hybridization efficiency of 100%, however, the intensity of the light emission of the marker sites 3 may be set so as to correspond to an optional value (for example, 10%, 1%, and so forth).

Further, the invention is also applicable to a case where target molecules bonded to the probe sites are amplified by PCR (Polymerase Chain Reaction). In this case, by controlling an amplification factor of PCR, and a ratio of the DNA with a fluorescent molecule bonded thereto, respectively, at the time of amplification, respective hybridization efficiencies at the probe sites 2 can be found on the basis of an intensity of light of the marker sites 3.

Still further, with the present embodiment described as above, the fluorescent molecule is pre-added to the target molecules, respectively, before the hybridization, however, the invention is also applicable to a case where the fluorescent molecule is added to the target molecules, respectively, after the hybridization. The invention is also applicable to, for example, a process whereby the target molecules are marked with biotin, and after the hybridization, a fluorescent molecule with avidin bonded thereto is added to the target molecules, respectively.

Yet further, with the present embodiment described as above, the fluorescent molecule 6 is pre-added to the respective marker sites 3, respectively, however, a procedure may be changed such that a user of the biochip causes the fluorescent molecule to be bonded to the respective marker sites, in a predetermined stage. For example, DNA with biotin added thereto are disposed at the respective marker sites during formation of the biochip, and at the time of using the biochip, for example, after the hybridization, the fluorescent molecule with avidin added thereto is bonded to the respective marker sites.

The invention is also applicable to a dichromic method (competitive hybridization method). In this case, the respective marker sites may be formed by spotting with mixture of DNA modified with fluorohores respectively emitting fluorescent light rays in two colors.

Further, it is to be understood that the invention is not limited in scope of application to the embodiments described in the foregoing. The invention is widely applicable to a biochip utilizing the principle of the hybridization, and the analytical instrument for analyzing the biochip.

What is claimed is:

1. A method for analyzing a biochip on which a plurality of probe sites with target molecules to be bonded thereto, respectively, and marker sites with a known number of intensity of fluorescent light emission, respectively, are disposed, said method comprising:
    irradiating the biochip with excited light;
    capturing respective intensity of fluorescent light emission from the probe sites, and respective intensity of fluorescent light emission from the marker sites, at the time of irradiation of the biochip with the excited light; and,
    quantitatively measuring respective hybridization efficiencies of the probe sites, by comparing the respective intensity of fluorescent light emission of the probe sites, as captured, with the respective intensity of fluorescent light emission of the marker sites, as captured.

2. A method according to claim 1, further comprising positioning capturing regions on the basis of the fluorescent light from the respective marker sites.

* * * * *